United States Patent
Grinberg

(10) Patent No.: US 8,034,033 B2
(45) Date of Patent: Oct. 11, 2011

(54) HYPODERMIC SYRINGE WITH VIAL ATTACHMENT

(76) Inventor: Yair Grinberg, New Preston, CT (US)

( * ) Notice: Subject to any disclaimer, the term of this patent is extended or adjusted under 35 U.S.C. 154(b) by 22 days.

(21) Appl. No.: 11/766,916

(22) Filed: Jun. 22, 2007

(65) Prior Publication Data

US 2008/0255515 A1 Oct. 16, 2008

Related U.S. Application Data

(60) Provisional application No. 60/911,634, filed on Apr. 13, 2007.

(51) Int. Cl.
*A61M 3/00* (2006.01)
(52) U.S. Cl. ............ 604/189; 604/187; 604/232
(58) Field of Classification Search .......... 604/111, 604/181, 187, 189, 232, 234, 200, 201, 205, 604/235; 206/364, 363, 366, 368–370, 210; 248/229.17, 230.8, 311.2; 433/49, 163, 50
See application file for complete search history.

(56) References Cited

U.S. PATENT DOCUMENTS

| | | | |
|---|---|---|---|
| 0,612,296 A | 10/1898 | Woodward | |
| 836,033 A | 11/1906 | Handy | |
| 2,627,269 A * | 2/1953 | Mcgregor | 604/2 |
| 3,113,693 A * | 12/1963 | Stull | 220/792 |
| 3,881,677 A * | 5/1975 | Ihlenfeld | 248/311.2 |
| 3,994,295 A | 11/1976 | Wulff | |
| 4,342,310 A | 8/1982 | Lindmayer et al. | |
| 4,911,693 A | 3/1990 | Paris | |
| 5,067,948 A | 11/1991 | Haber et al. | |
| 5,084,021 A | 1/1992 | Baldwin | |
| 5,169,385 A | 12/1992 | Turnbull | |
| 5,195,983 A | 3/1993 | Boese | |
| 5,290,261 A * | 3/1994 | Smith et al. | 604/234 |
| D363,017 S | 10/1995 | Noble | |
| D363,211 S | 10/1995 | Noble | |
| 5,498,245 A | 3/1996 | Whisson | |
| 5,755,415 A | 5/1998 | Sorg | |
| 5,873,859 A * | 2/1999 | Muntz | 604/207 |
| 6,027,472 A | 2/2000 | Kriesel et al. | |
| 6,102,258 A | 8/2000 | Riley et al. | |
| 6,183,249 B1 * | 2/2001 | Brennan et al. | 433/9 |
| 6,269,985 B1 | 8/2001 | Brody | |
| 6,565,054 B2 | 5/2003 | Weesner et al. | |
| 6,808,149 B1 * | 10/2004 | Sendowski et al. | 248/311.3 |
| 2002/0083564 A1 * | 7/2002 | James | 24/336 |
| 2003/0187410 A1 | 10/2003 | Erickson | |
| 2003/0208167 A1 | 11/2003 | Prausnitz et al. | |
| 2003/0236501 A1 | 12/2003 | Donnan et al. | |
| 2004/0168293 A1 | 9/2004 | Shimazaki | |
| 2006/0032768 A1 * | 2/2006 | Hamai et al. | 206/364 |
| 2006/0166170 A1 * | 7/2006 | Masters | 433/215 |
| 2006/0236913 A1 * | 10/2006 | Wills | 116/206 |
| 2007/0173775 A1 * | 7/2007 | Fletcher | 604/232 |
| 2009/0020597 A1 * | 1/2009 | D'Amato | 229/403 |

OTHER PUBLICATIONS

"Adhesive". Merriam-Webster Online Dictionary. <http://www.merriam-webster.com/dictionary/adhesive>.* International Search Report.

* cited by examiner

*Primary Examiner* — Theodore Stigell
*Assistant Examiner* — Kami A Bosworth
(74) *Attorney, Agent, or Firm* — F. Chau & Associates, LLC

(57) ABSTRACT

A medical syringe apparatus includes a syringe unit, a hypodermic needle attached to the syringe unit and at least one interfacing member for mating a labeled medication container to the syringe unit. The medication label is visible. The container remains mated to the syringe when the syringe is in use. Risk of mislabeling the syringe may therefore be substantially reduced or eliminated and patient safety may accordingly be improved.

26 Claims, 12 Drawing Sheets

HYPODERMIC SYRINGE WITH VIAL ATTACHMENT

CROSS-REFERENCE TO RELATED APPLICATION

The present application is based on provisional application Ser. No. 60/911,634, filed Apr. 13, 2007 the entire contents of which are herein incorporated by reference.

BACKGROUND OF THE INVENTION

1. Technical Field

The present disclosure relates to hypodermic syringes and, more specifically, to hypodermic syringes with vial attachment.

2. Discussion of the Related Art

In the course of administering medication to a patient by hypodermic injection, a syringe is filled from a vial of medication. While the vial is generally pre-labeled according to its contents, the syringe is generally unlabeled when removed from sterile wrapping. Medical practitioners such as physicians, nurses and medical technicians, may take the time to manually label a syringe after drawing medication from a vial. A syringe that is so-labeled reduces the chance of administering an incorrect medication, an occurrence that is commonly known as syringe swap error.

Syringe swap error may be a particular risk in the field of anesthesiology where multiple different medications are used and a particular medication may be called upon at a moment's notice. For example, some medications must be administered in rapid succession.

Multiple medications may be drawn up in multiple syringes and labeled in the course of preparing for a surgical case, however this process may be time consuming and may itself be prone to error. In the real-world setting, medical practitioners may be unwilling and/or unable to take the time to properly label each syringe. Moreover, in manually labeling each syringe, labeling errors may occur, especially where labels are written hastily. Additionally, manually labeled syringes may not be readily legible.

Manual labeling may give rise to other potential problems, for example, the type of medication may be labeled but other information such as the concentration, the inactive ingredients, and the expiration date may be omitted. Such information may even be intentionally omitted from the syringe labels but may later be needed in order to quickly determine the cause of a problem in the event of complications, at which point, the vial may have since been deposited in a sharps container and may be irretrievable.

Labels may be preprinted in an attempt to minimize some of the problems discussed above; however, preprinted labels may be mistakenly applied to the wrong syringe. Moreover, the use of adhesive labels may be problematic when working with gloved hands, as is generally the case in operating rooms.

Syringes may be pre-labeled at the time of assembly; however, pre-labeled syringes are significantly less versatile as a syringe pre-labeled for one medication may not be used to administer another medication. Accordingly, hospitals and other medical facilities must stock enough syringes for each type of medication used. Accordingly, the costs of procuring, storing and retrieving the correct pre-labeled syringe may be inordinately expensive. Moreover, the incorrect pre-labeled syringe may be inadvertently used.

SUMMARY

A medical syringe apparatus includes a syringe unit, a hypodermic needle attached to the syringe unit and at least one interfacing member for mating a labeled medication container to the syringe unit. The medication label is visible. The container remains mated to the syringe when the syringe is in use.

A method for labeling a syringe includes inserting a hypodermic needle of the syringe into a labeled container of medication. Medication is drawn from a container into the syringe. The hypodermic needle is removed from the container. The container is mated to the syringe such that the label of the container is visible and such that the container remains mated to the syringe when the syringe is in use.

A medical syringe apparatus includes a syringe unit and at least one interfacing member for removably mating a labeled medication container to the syringe unit. The medication label is visible. The container remains mated to the syringe when the syringe is in use. The interfacing unit accommodates the container irrespective of the size of the container by either adjusting to accommodate the size of the container or by having multiple interfacing members with each interfacing member for accommodating a container of a different size.

A hypodermic injection unit includes a syringe. A hypodermic needle is attached to the syringe. The hypodermic injection unit further includes an indicator pad for changing a visual state when exposed to a change in ambient conditions.

BRIEF DESCRIPTION OF THE DRAWINGS

A more complete appreciation of the present disclosure and many of the attendant advantages thereof will be readily obtained as the same becomes better understood by reference to the following detailed description, when considered in connection with the accompanying drawings, wherein.

DETAILED DESCRIPTION OF EXEMPLARY EMBODIMENTS

Figure 1:
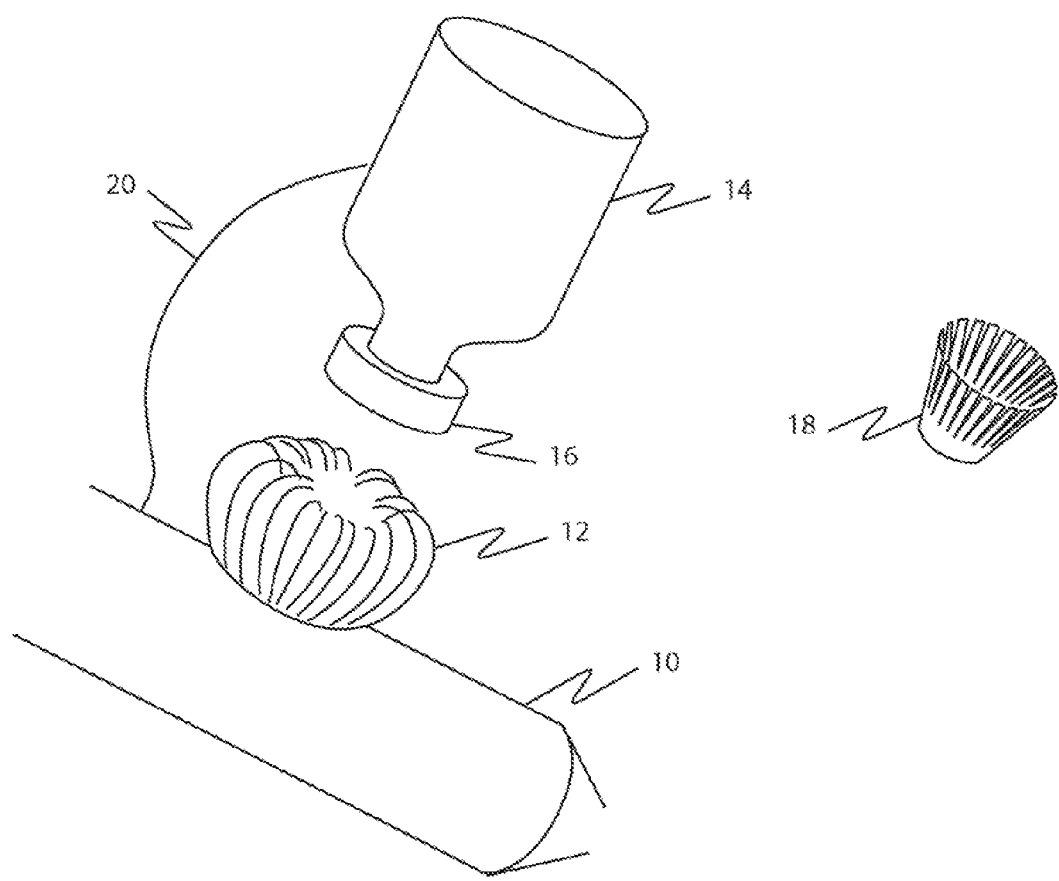
FIG. 1 illustrates a syringe capable of mating with a medicine container according to an exemplary embodiment of the present invention.

In describing the exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention relate to a syringe, for example, a hypodermic syringe, which may be mated to a medication container, for example, an ampule or vial. After drawing medication from the vial into the syringe, the medical practitioner may mate the used vial to the syringe. By mating the medication vial to the syringe, medical practitioners may be able to easily determine the contents of the syringe by reading the label on the medication vial.

According to some exemplary embodiments of the present invention, the vial may be mated to the syringe by an interfacing member incorporated with the syringe. The interfacing member may lock the vial in place using friction forces and/or an adhesive coating. In some exemplary embodiments, the vial may be permanently affixed to the syringe. In other exemplary embodiments, the vial may be removably affixed to the syringe, for example, to allow for additional medication to be drawn from the vial at a latter point and to allow for subsequent reattachment of the vial to the syringe. Where the vial is removably affixed, a tethering connector may be used to ensure physical proximity and to minimize the risk of the wrong vial being affixed to the syringe.

A user, for example a medical practitioner, may mate the vial to the syringe after drawing medication from the vial into the syringe. After the medication has been drawn, the user may be holding the syringe in one hand and the vial in the other hand. Accordingly, the vial may be quickly and easily mated to the interfacing member of the syringe after the medication has been drawn. Where multiple syringes are used to draw medication from multiple corresponding vials, the user may easily draw medication and mate the corresponding vial to the syringe before the syringe and vial are put down. Accordingly, multiple medications may be drawn into multiple corresponding syringes and the syringes may be labeled by mating the corresponding vial to the corresponding syringe with little to no risk of label confusion.

Exemplary embodiments of the present invention contemplate various interfacing members including snapping locks, clamping locks, tying locks, ratchet locks, twist locks, buckle locks, adhesive pads, and the like. According to some exemplary embodiments, a single syringe may include multiple interfacing members for holding multiple vials simultaneously, where a single syringe contains multiple medications. Alternatively, the multiple interfacing members may be used to hold a single vial and the multiple interfacing members are each suitable for mating a vial of a different size and/or shape.

The figures and the disclosure below describe various exemplary embodiments of the present invention having various features. It should be understood that the features described with respect to one exemplary embodiment may be combined with features described with respect to other exemplary embodiments.

FIG. 1 illustrates a syringe capable of mating with a medicine container according to an exemplary embodiment of the present invention. In FIG. 1, the syringe 10 may have an interfacing member for mating a medication vial 14 to the syringe 10. The interfacing member may be, for example, a clamping unit 12. The clamping unit 12 may include a material that can flex and exert a restoring force, for example, a plastic or a shape memory alloy. Accordingly, a portion of the vial 14, for example a cap 16 of the vial 14, may be inserted into the clamping unit 12 and may be held in place by friction forces. The clamping unit 12 may be arranged to allow for the vial 14 cap 16 to be inserted and to prevent easy removal. This may be accomplished, for example, by including a plurality of flexors that are bent inwards, as shown. Alternatively, the interfacing member may be a clamping unit 18 including a plurality of flexors that are not bent inwards so that insertion, removal and reinsertion may be more easily accommodated.

In some exemplary embodiments of the present invention, a tether 20 is provided to link the syringe 10 to the vial 14, even when the vial 14 is not mated. The tether 20 may be a flexible material such as plastic, latex, string, wire or the like. The tether 20 may attach to the vial by, for example, an adhesive measure or by friction. For example, the tether 20 may have a rubber hand, loop for holding the vial 14. Alternatively, the tether 20 may include a plastic tie-wrap, also known as a zip tie, for holding the vial 14. The tether 20 may secure the vial at its body, as shown, or the tether 20 may secure the vial at its neck.

Alternatively, the vial 14 may be glued, taped, snapped or screwed to the syringe 10. In such exemplary embodiments, the interfacing member may be the selected adhesive mechanism. The interfacing member may be attached to the syringe 10 during manufacture; alternatively, the interfacing member may be formed as part of the syringe 10, for example, during an injection molding process, extrusion process or some other manufacturing process.

According to an exemplary embodiment of the present invention, the interfacing member may be an adhesive pad attached to the syringe 10. The adhesive pad may be covered with a protective film that may be easily removed when coupling to a vial is desired.

Figure 2:
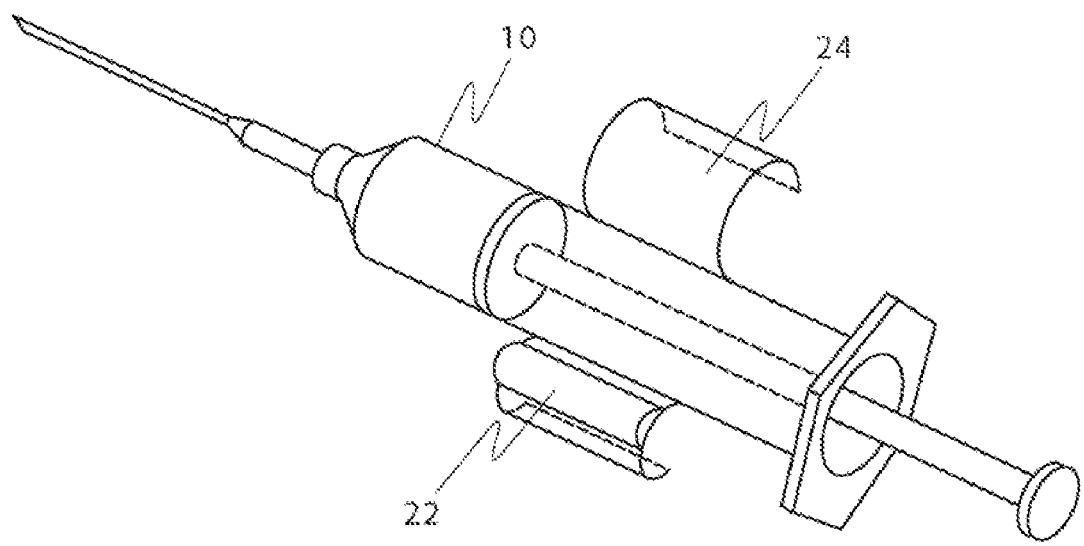
FIG. 2 illustrates a syringe having multiple interfacing members for mating with medicine containers of various sizes according to an exemplary embodiment of the present invention.

As discussed above, exemplary embodiments of the present invention may have multiple interfacing members for mating either multiple medication containers at the same time or for mating one of a variety of differently sized containers. FIG. 2 illustrates a syringe having multiple interfacing members for mating with medicine containers of various sizes according to an exemplary embodiment of the present invention. In FIG. 2, the syringe 10 includes a first interfacing member 22 and a second interfacing member 24. While some exemplary embodiments of the present invention may have multiple interfacing members of the same size, FIG. 2 shows an exemplary embodiment having multiple interfacing members of differing sizes. While some exemplary embodiments may have one, two, three or more interfacing members, FIG. 2 shows an exemplary embodiment having two interfacing members.

The first interfacing member 22 may be a small-sized interfacing member for mating to small ampules or vials. The second interfacing member 24 may be a large-sized interfacing member for mating to large ampules or vials. The interfacing members 22 and 24 shown in FIG. 2 are examples of clasps that grab and hold medicine containers by either squeezing tightly around the perimeter of the vial or by adhering to the surface of the vial; however, multiple interfacing members may be of other forms as well.

Rather than having multiple interfacing members for holding containers of various sizes, a single adjustable interfacing member may be used. For example, the interfacing member could be a spiral shaped arm of plastic or memory alloy that may flex to accommodate containers of various sizes.

Figure 3:
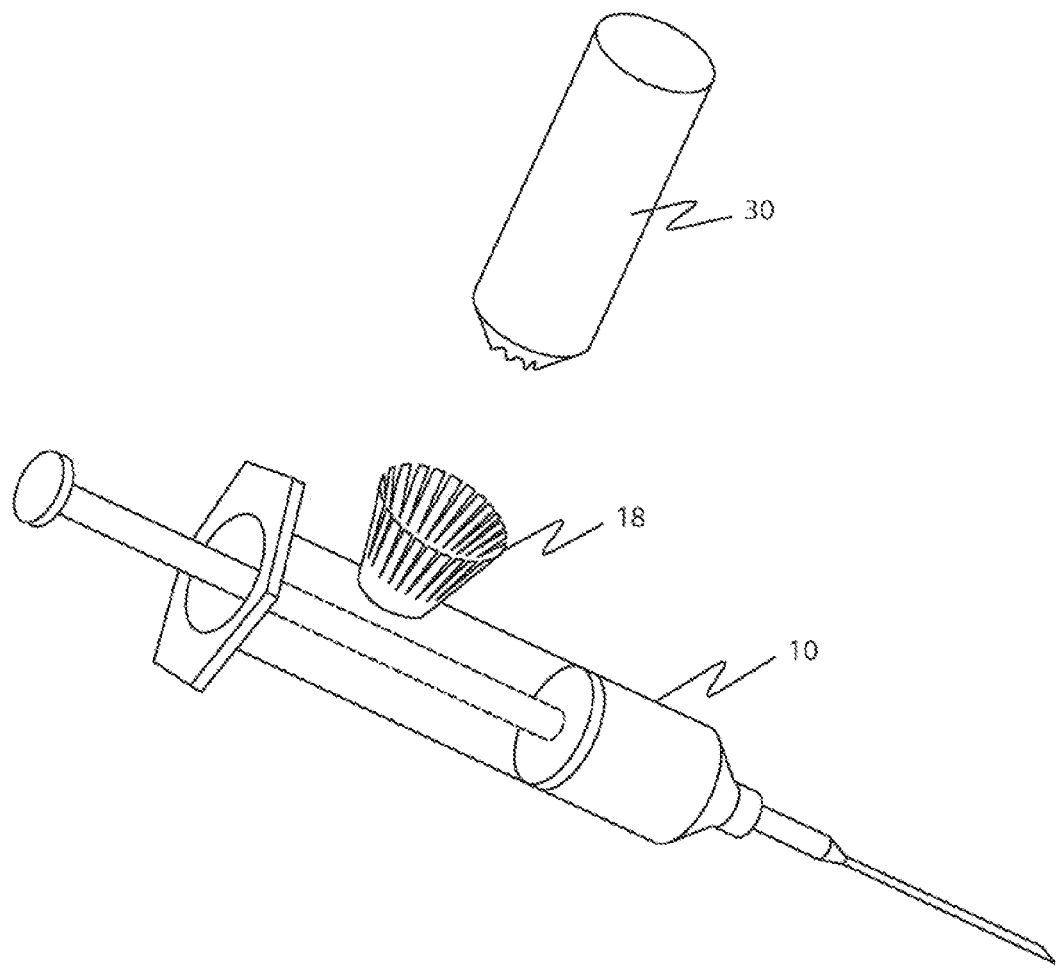
FIG. 3 illustrates a syringe capable of mating with a medicine container, for example, an ampule 30 with a sharp end, while protecting the medical practitioner from risk of accidental contact with the sharp end, according to an exemplary embodiment of the present invention.

Ampules are containers of medication that may be broken open. Accordingly, after having been opened, ampules may have a sharp end of broken glass. Exemplary embodiments of the present invention may mate with open ampules in such a way as to protect the medical practitioner from risk of accidental contact with the sharp end of open ampules. FIG. 3 illustrates a syringe capable of mating with a medicine container, for example, an ampule 30 with a sharp end, while protecting the medical practitioner from risk of accidental contact with the sharp end, according to an exemplary embodiment of the present invention. As seen in FIG. 3, the syringe having a clamping unit 18 as an interfacing member. The clamping unit 18 may conceal the sharp end of the ampule 30 after it is snapped in place.

Figure 4:
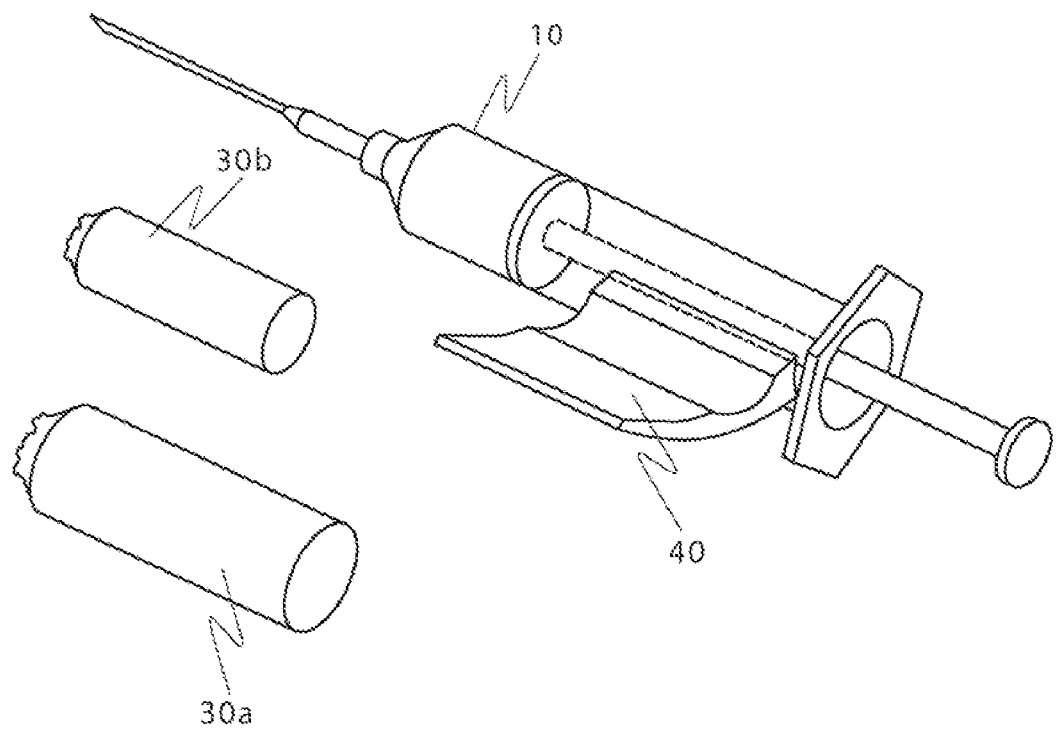
FIG. 4 illustrates a syringe including an adhesive cup as an interfacing member according to an exemplary embodiment of the present invention.

According to another exemplary embodiment of the present invention illustrated in FIG. 4, the syringe 10 may include an adhesive cup 40 as an interfacing member. The adhesive cup 40 may have a concave surface to receive the container. The adhesive cup 40 may be flexible to allow for a tail end of the adhesive cup to wrap around the vial for additional adhesive contact. The adhesive cup 40 may be made of, for example, a soft plastic or foam material. Alternatively, the adhesive cup 40 may be ridged. The adhesive cup 40 may comprise a contoured arm covered by adhesive glue for mating with the container. The adhesive cup 40 may be strongly adhesive to prevent removal of the container or may be less-strongly adhesive to allow for removal and replacement of the container.

Alternatively, a removably adhesive device, for example, VELCRO strips, may be provided on the adhesive cup 40. For example, a first VELCRO strip may be provided upon the adhesive cup 40 and a second VELCRO strip that is capable of mating with the first VELCRO strip may be provided, in a mated state, upon the first VELCRO strip. The second VELCRO strip may then have an adhesive surface for mating with the container. Accordingly, a container mated with the adhesive surface may be freely removable from the adhesive cup 40 and replaceable by virtue of the VELCRO strip. Alternatively, the first VELCRO strip may be provided directly on the body of the syringe instead of on the adhesive cup 40.

In such embodiments, VELCRO is mentioned as an example of a suitable reachable fastener, however, other mating fasteners such as snaps and magnetic devices may be used.

The adhesive surface of the adhesive cup 40 or second VELCRO strip may be covered by a protective film to protect the adhesive surface when contained in its sterile packaging. The concave surface may have an irregular concavity to allow for the holding of different sized containers, for example, a large ampule 30a or a small ampule 30b. For example, the concavity may have a large radius at one end and have a small radius at the other end. Flexibility may also facilitate the holding of different sized containers.

Figure 5:
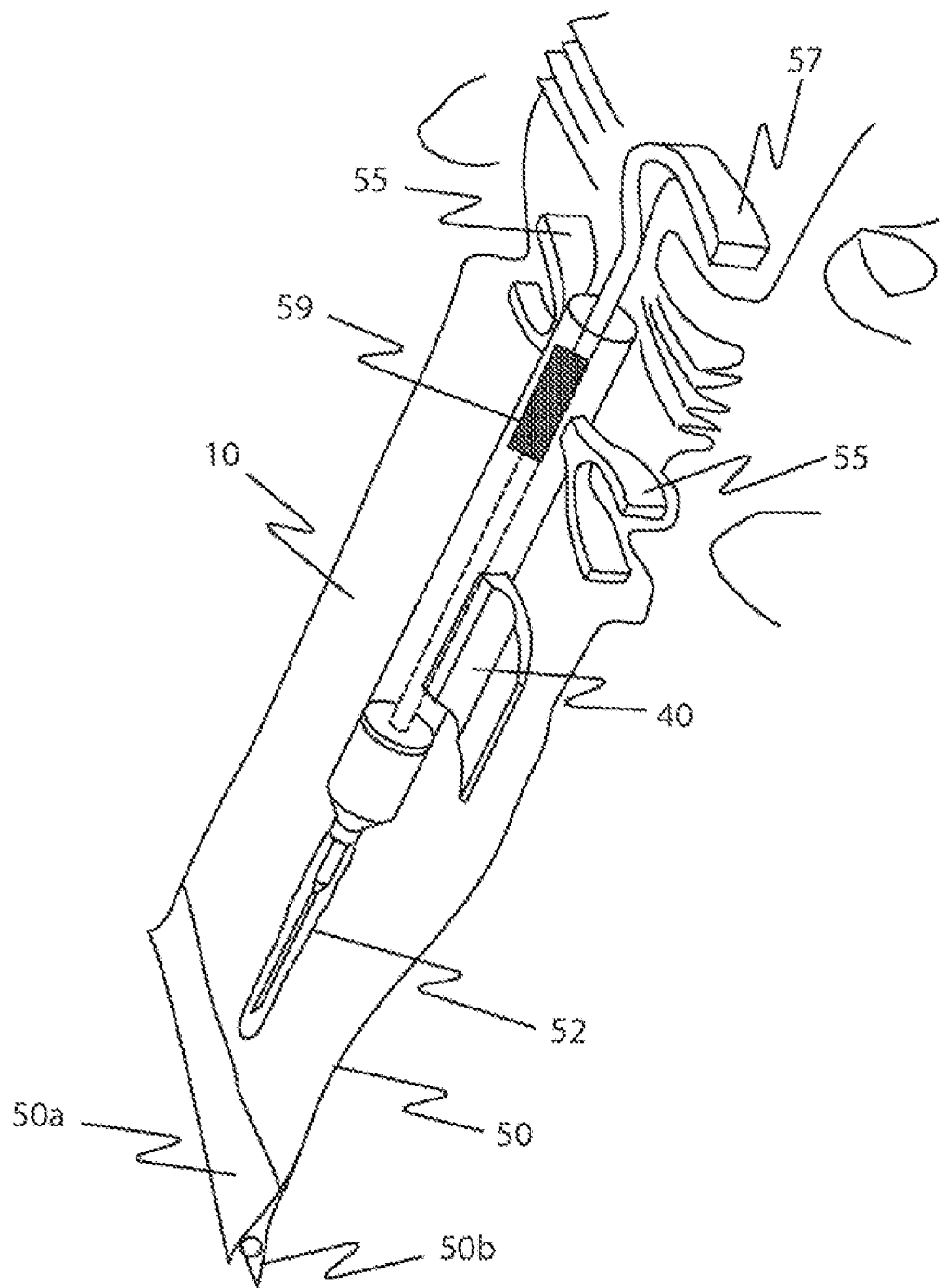
FIG. 5 illustrates a syringe capable of mating with a medicine container according to an exemplary embodiment of the present invention.

For exemplary embodiments having an adhesive surface, either directly on the adhesive cup 40 or on a second VELCRO strip, the protective film that protects the adhesive surface may be coupled to the sterile packaging of the syringe such that when the sterile packaging is removed, so too is the protective film. For example, the protective film may be attached to the sterile packaging or, for example, the sterile packaging may itself protect the adhesive surface. FIG. 5 illustrates a syringe capable of mating with a medicine container according to an exemplary embodiment of the present invention. In FIG. 5, the syringe is packaged in a sterile packaging 50. The sterile packaging 50 may be, for example, a two-layer peel pack including an upper layer 50a and a lower layer 50b. The upper layer 50a may be transparent; the lower layer 50b may be shrink-wrapped around the flanges 55 of the syringe 10. The syringe 10 may include an adhesive cup 40 with an adhesive top surface. A layer of the sterile packaging 50, for example, the upper layer 50a may be pressed against the adhesive top surface of the adhesive cup 40.

When opening the sterile packaging 50, the medical practitioner may grip the syringe 10 in the sterile packaging 50 in the vicinity of the flanges 55 and a hook-end 57 while a needle-end 52 of the syringe 10 is unpackaged. The medication may then be drawn from a vial prior to unpackaging the remainder of the syringe 10. When the remainder of the syringe 10 is unpackaged, the upper layer 50a may be pulled from the adhesive cup 40 thus exposing the adhesive top surface. The vial of medication used to fill the syringe may then be adhered to the adhesive cup 40, for example, in the manner discussed above. As discussed above, the adhesive cup 10 may utilize a permanent adhesive for irremovably attaching the vial to the adhesive cup 40 or a milder adhesive may be used for removably attaching the vial to the adhesive cup 40. Embodiments allowing for removal may incorporate the use of a tether for maintaining a link between the vial and the syringe even when the vial is in a removed state.

The syringe 10 may also include an indicator pad 59. The indicator pad 59 may be used to indicate whether the sterile packaging 50 has been opened and/or for how long the packaging 50 has been opened. According to one exemplary embodiment of the present invention, the indicator pad 59 is capable of changing color when removed from the packaging 50. For example, the indicator pad 59 may include a color-change die that changes from one color to another color when exposed to ambient air and/or ambient light. For example, the color-change die may change color to reflect oxidation as the die is exposed to oxygen in the atmosphere. In such a case, the sterile packaging 50 may be packaged in an oxygen-free environment, such as a vacuum or an environment filled with an inert gas such as nitrogen.

Alternatively, the color-change die may change color when exposed to ambient light. In such a case, an opaque covering may conceal the indicator pad 59 while the syringe 10 is packaged. When the syringe 10 is removed, the opaque covering may be simultaneously removed. For example, the opaque covering may be part of or otherwise coupled to the packaging 50. The opaque covering may also be, or may alternatively be a gas-impermeable protective covering that protects the indicator pad 59 from exposure to the air within the packaging 50. This may allow the syringe to be packed in an oxygen environment without initiating color change in the indicator pad 59.

The indicator pad 59 may have a single color change state that is initiated during a single exposure to ambient conditions. In such a case, the indicator pad 59 indicates whether the packaging has been opened. Alternatively, the indicator pad 59 may have multiple color change states, or may otherwise continuously change as ambient exposure increases. In such a case, the length of time the syringe 10 has been unpackaged for may be readily determined by examining the state of the indicator pad 59.

The indicator pad 59 may change color in a single section or may include multiple sections that change color at different exposure durations. Each section may be a geometric shape or may form lettering and/or numbering that helps to communicate the state of the indicator pad 59. Additional lettering and instructions may be printed on the syringe 10 to help the user interpret the color change.

Figure 6:
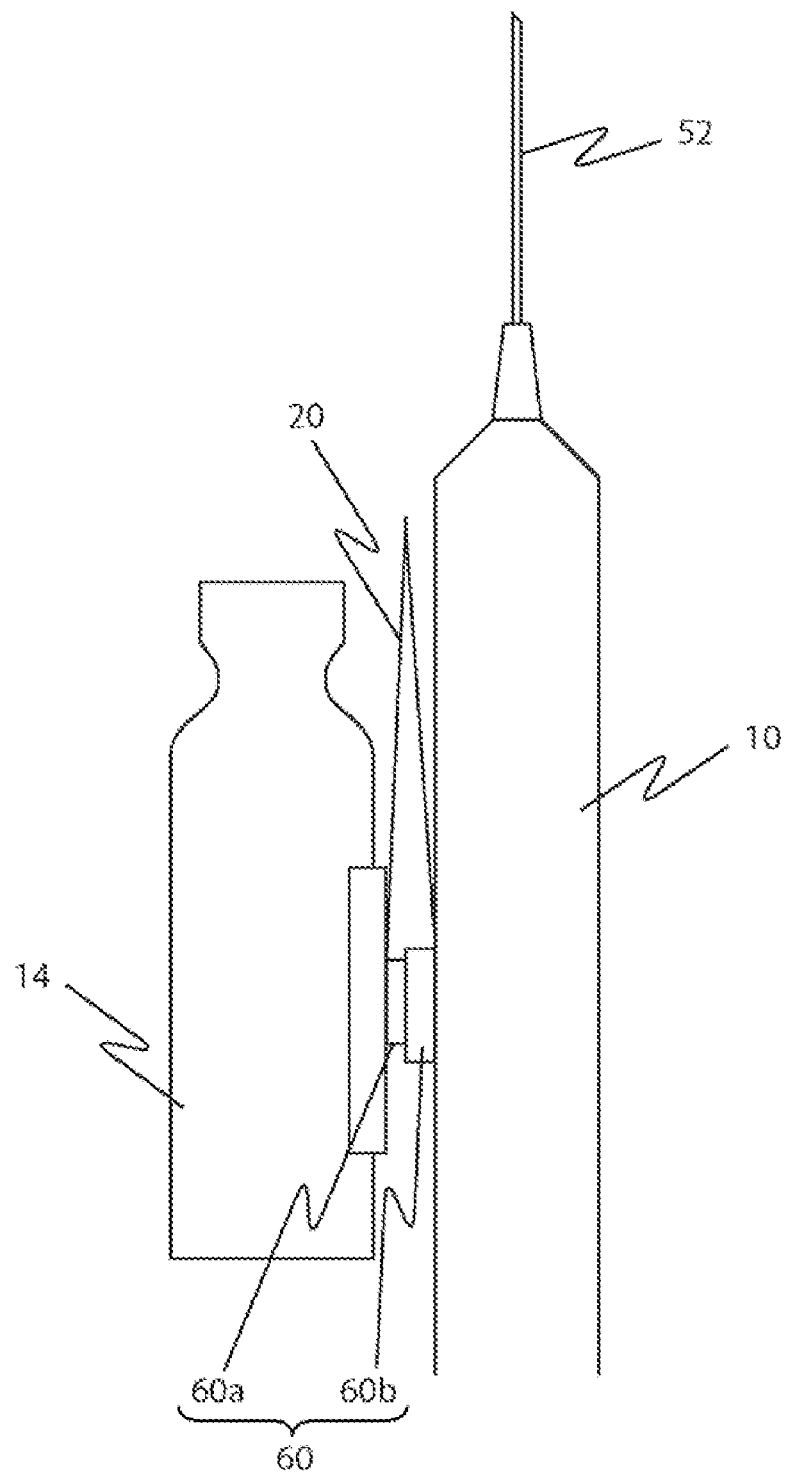
FIG. 6 illustrates a syringe attached to a vial via a locking member according to an exemplary embodiment of the present invention.

FIG. 6 shows a syringe 10 attached to a vial 14 via a locking member 60 according to an exemplary embodiment of the present invention. The locking member includes an upper-portion 60a that may be attached to the vial, for example, by an adhesive, and a lower-portion 60b that may be attached to the syringe. The upper-portion 60a and the lower portion 60b removably interlock, for example, by snapping, adhesiveness and/or by magnetic members. A tether 20 may connect the syringe 10 and the vial 14 even when the vial 14 is detached. The tether 20 may be connected, at one end, either to the syringe 10 or to the lower-portion 60b of the locking member 60. The tether 20 may be connected, at the other end, to the upper-portion 60a of the locking member 60. By connecting the tether 20 to the upper-portion 60a, the medical practitioner does not have to affix the tether 20 to the vial 14. The tether 20 may be long enough to allow the needle 52 to be inserted into the vial 14 during filling.

Figure 7:
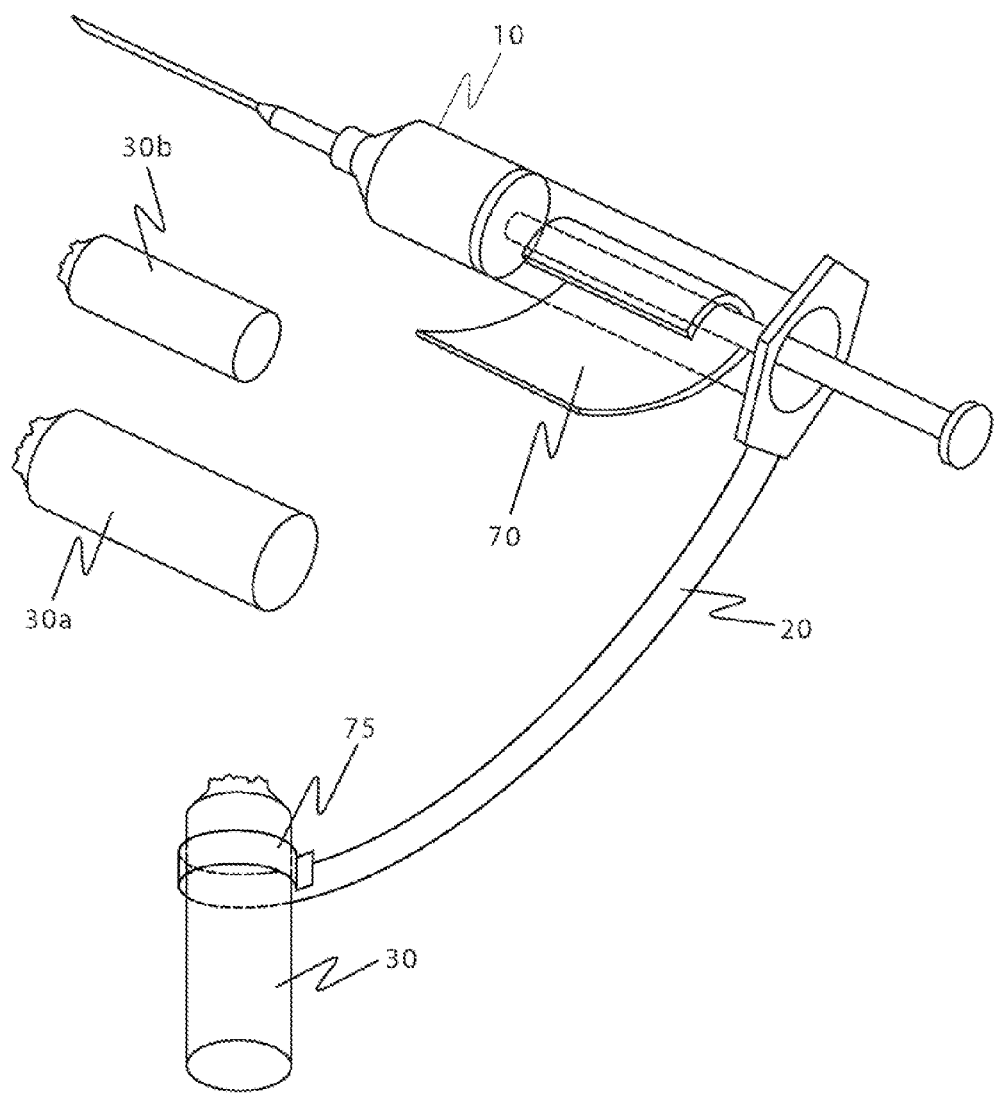
FIG. 7 illustrates a tether connecting a syringe with a container according to an exemplary embodiment of the present invention.

According to an exemplary embodiment of the present invention shown in FIG. 7, the tether 20 may include a band that connects to the syringe 10 at one end and terminates in a loop 75 at the other end. The loop 75 may close upon the container 30, for example, by including a zip-tie. The loop 75 may be adjustable to accommodate containers 30 of various sizes, for example, a small container 30b or a large container 30a. The interfacing member may be a fastening loop 70 that may either adhere to the container 30 and/or lock around the container 30. The fastening loop may be flexible and may thus accommodate containers of various sizes.

The syringe may also be configured to count the number of vials that have been attached and then removed. This may be accomplished, for example, by utilizing a multi-layered adhesive surface on the adhesive cup such that every time a vial is removed from the adhesive cup, the vial takes with it one of the adhesive layers. The number of vials removed from the syringe may then be determined from the number of layers that have been removed from the adhesive cup. Each layer may be numbered such that the number clearly indicates to the medical practitioner how many layers have been removed, and thus, how many vials have been attached to the adhesive cup. To prevent more than, one such layer from, being removed with a single vial, the various layers may be adhered to differing degrees or another method known in the art may be used. This feature may be especially useful where multiple vials of medication are used with a single syringe.

Figure 8:
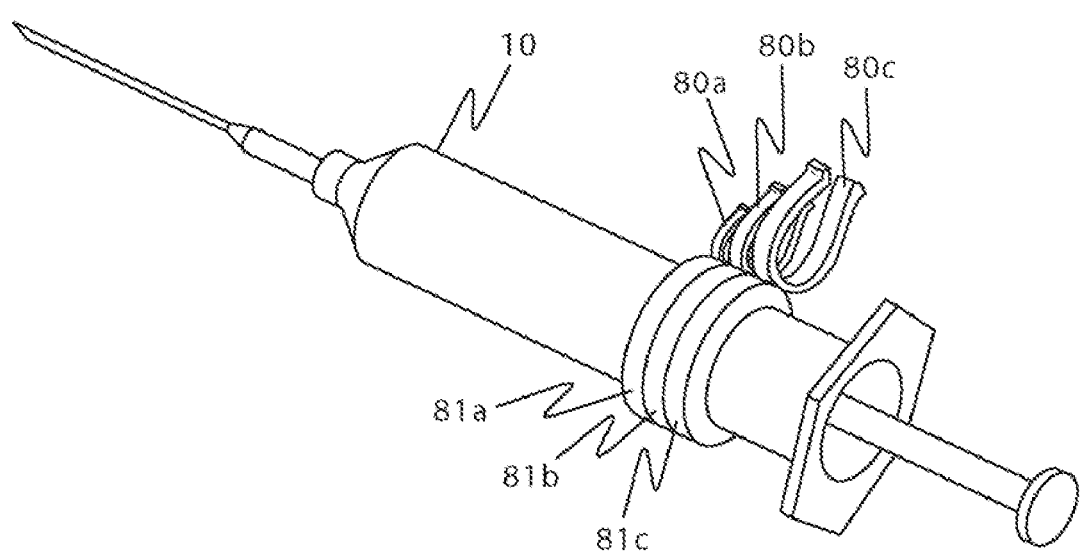
FIG. 8 illustrates a syringe including multiple interfacing members according to an exemplary embodiment of the present invention.

Exemplary embodiments of the present invention may utilize any number of interfacing members. FIG. 8 shows a syringe including multiple interfacing members according to an exemplary embodiment of the present invention. As shown in FIG. 8, the syringe 10 may include multiple interfacing members 80a, 80b, and 80c of differing sizes so that variously sized containers may be properly accommodated. The interfacing members 80a, 80b, and 80c may each rotate so that the unused interfacing members may be rotated so as not to obstruct the placement of the vial. Each of the interfacing members shown in this figure are horseshoe shaped and a at least somewhat flexible to allow for a cylindrical vial to snap into place; however, other designs are possible. The interfacing members 80a, 80b, and 80c are each attached to corresponding rings 81a, 81b, and 81c and are thus free to rotate about the syringe 10 shaft.

Figure 9:
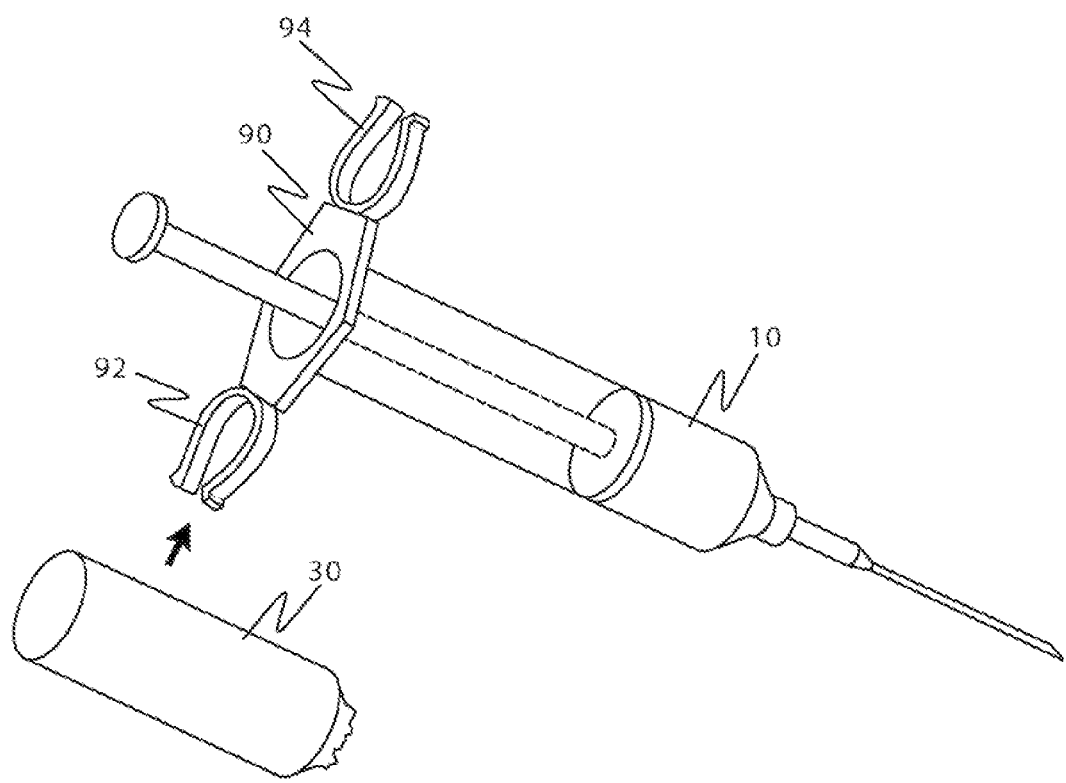
FIG. 9 illustrates a syringe with integrated interfacing members according to an exemplary embodiment of the present invention.

As shown in FIG. 8, the interfacing members may be formed of parts that are added to the syringe apparatus during assembly. Alternatively, the interfacing members may be manufactured as part of the syringe. FIG. 9 shows a syringe with integrated interfacing members according to an exemplary embodiment of the present invention. In FIG. 9, the interfacing members include a first interfacing member 92 and a second interfacing member 94 that are each formed as part of the syringe 10 flange 90. Each interfacing member 92 and 94 are shown as being horseshoe shaped, however other configurations are contemplated. Two interfacing members are shown, however, there may be any number of interfacing members, for example, there may be one, two, three, or four interfacing members. Each of the interfacing members may be configured to accommodate a container 30 of a different size. For example, interfacing member 92 may accommodate a smaller container while interfacing member 94 may accommodate a larger container.

Figure 10:
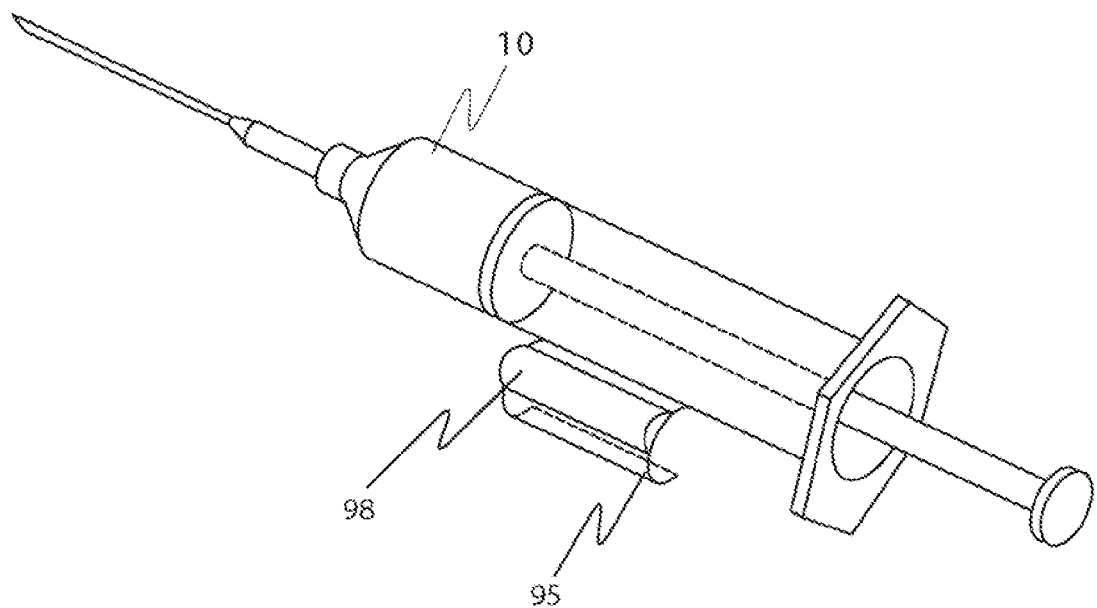
FIG. 10 illustrates a syringe include an interfacing member for mating a container of medication where the interfacing member includes a magnifying member for magnifying a label of the container of medication according to an exemplary embodiment of the present invention.

FIG. 10 illustrates a syringe including an interfacing member for mating a container of medication where the interfacing member includes a magnifying member for magnifying a label of the container of medication according to an exemplary embodiment of the present invention. Here, the syringe 10 may include an interfacing member 95, for example, as described above. However, the interfacing member 95 may additionally include a magnifying member 98, which may be, for example, a lens. The magnifying member 98 may magnify text of the container label and thus may make the contents of the container more easily read by the medical practitioner.

Figure 11A:
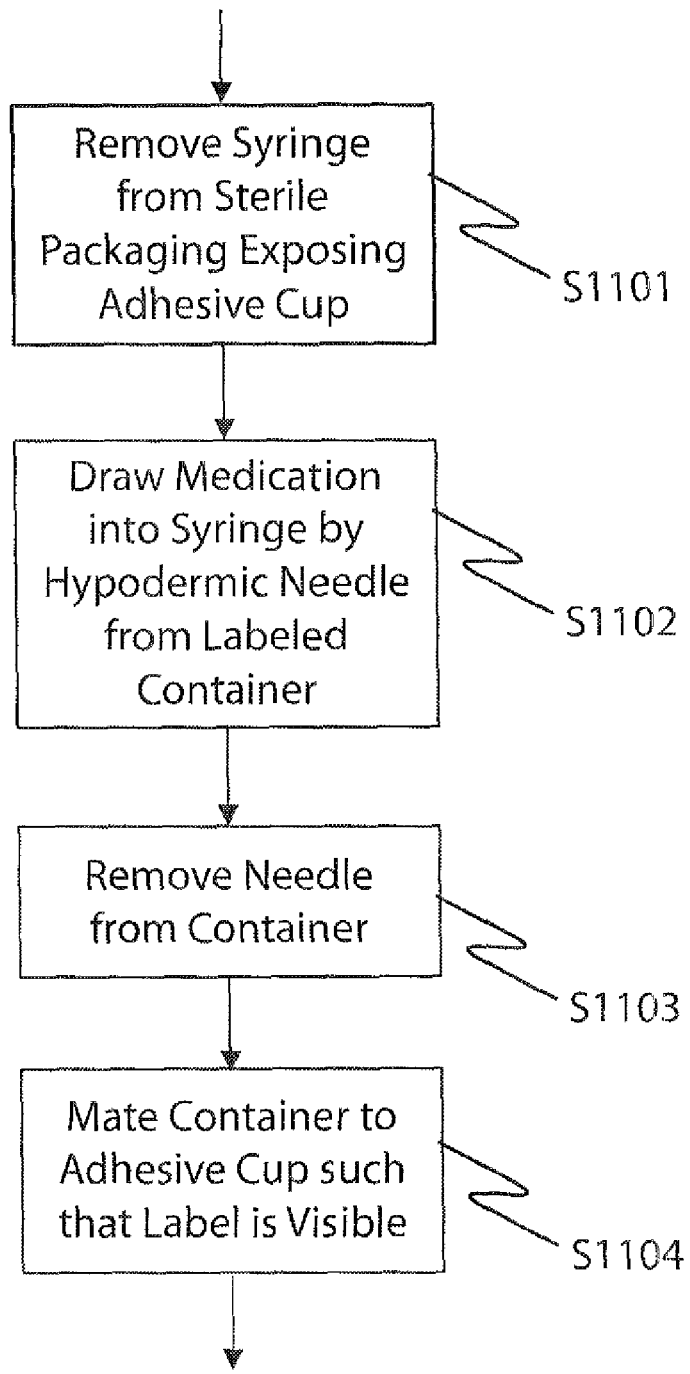
FIG. 11A illustrates a method for labeling a syringe according to an exemplary embodiment of the present invention.

FIG. 11A illustrates a method for labeling a syringe according to an exemplary embodiment of the present invention. Where the syringe is packaged in a sterile packaging as described above and illustrated in FIG. 5, the syringe may be removed from the sterile packaging (Step S1101). As described above, as the packaging is removed, an adhesive surface of an interfacing member, for example, an adhesive cup, may become exposed. A hypodermic needle attached to the syringe may be inserted into a labeled container of medication and medication may be drawn into the syringe (Step S31102). The needle may then be removed from the container (Step S31103) and the container may be mated to the interfacing member (Step S1104). The interfacing of the container to the interfacing member may include, for example, attaching the container to the adhesive cup, where the interfacing member is an adhesive cup.

Figure 11B:
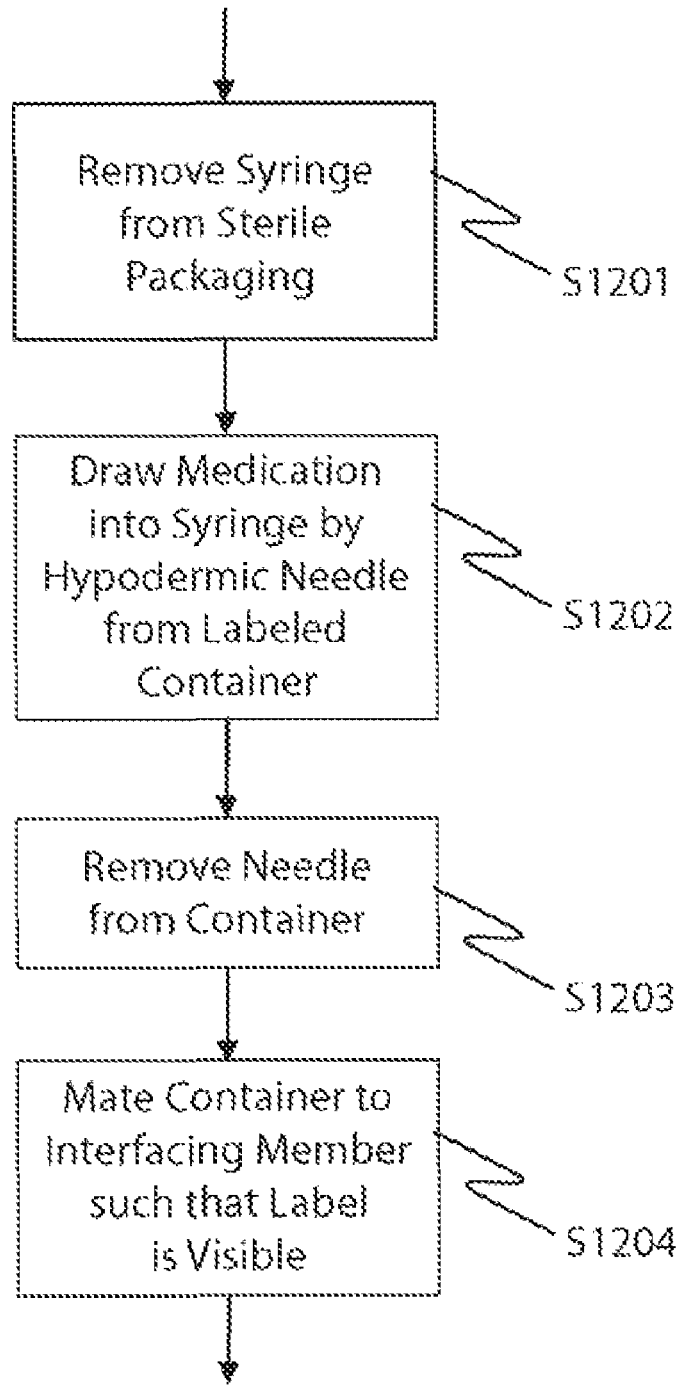
FIG. 11B illustrates another method for labeling a syringe according to an exemplary embodiment of the present invention.

Alternatively, it is to be understood that the interfacing member may alternatively include a configuration of any of the previously described embodiments to retain the container and that steps S1101 and S1104 may be in some embodiments so that the method proceeds as illustrated in FIG. 11B. The interfacing member may remain mated to the syringe when the syringe is in use. The interfacing member may non-detachably mate with the container such that the container may not be easily removed after mating. Alternatively, the interfacing member may detachably mate with the container such that the container may be removed and reattached, for example, when additional medication is to be drawn. In such cases, a tether may be used to retain a connection between the syringe and the container, even when the container is detached. The container may be mated to the interfacing member such that the label of the container is visible and the contents of the syringe are readily identifiable from the label.

According to exemplary embodiments of the present invention, the interfacing member may be a casing or bag member attached to the syringe. The casing or bag member may be either flexible or ridged and may contain a closing means such as a cap, draw string, twist tie, and/or zip lock. The casing or bag member may be transparent or may have at least a transparent window. Thus, a medication container may be placed in the casing or bag member when not in use, and a label of the container may be seen through the casing or bag member.

Exemplary embodiments of the present invention may substantially reduce or virtually eliminate the risk of mislabeling syringes that are filled with various medications. Accordingly, medication may be more safely administered to patients, for example, in an operating room setting. Therefore, the potential for complications resulting from administration of incorrect medication may be reduced and patient safety may accordingly be improved.

The above specific exemplary embodiments are illustrative, and many variations can be introduced on these embodiments without departing from the spirit of the disclosure or from the scope of the appended claims. For example, elements and/or features of different exemplary embodiments may be combined with each other and/or substituted for each other within the scope of this disclosure and appended claims.

What is claimed is:

1. A syringe unit, comprising:
  a syringe unit;
  a hypodermic needle attached to the syringe unit; and
  at least one interfacing member for mating a labeled medication container to the syringe unit such that the medication label is visible and unobstructed and such that the container remains mated to the syringe when the syringe is in use,
  wherein the interfacing member is an adhesive cup for receiving the container,
  wherein the adhesive cup does not completely surround the container 360 degrees, and
  wherein an outer surface of the adhesive cup is substantially planar with respect to a plane of symmetry shared by the medical syringe apparatus and the mated medication container when the adhesive cup is in an open or unwrapped state.

2. The apparatus of claim 1, wherein the interfacing member irremovably attaches the syringe unit to the container.

3. The apparatus of claim 1, wherein the interfacing member removably attaches the syringe unit to the container.

4. The apparatus of claim 1, wherein the adhesive cup includes a concave surface for receiving the container, the concave surface having an irregular concavity for holding different sized containers.

5. The apparatus of claim 4, wherein the adhesive cup is flexible to allow for the adhesive cup to wrap around containers of different sizes with the application of pressure to the adhesive cup.

6. The apparatus of claim 4, wherein the adhesive cup is flexible to allow for a tail end of the adhesive cup to wrap around containers of different sizes.

7. The apparatus of claim 1, wherein the interfacing member has a surface covered with an adhesive glue for adhering to the container.

8. The apparatus of claim 7, wherein the syringe apparatus is packaged in sterile packaging having an upper layer and a lower layer, and the upper layer is pressed against the adhesive surface prior to unpackaging the syringe apparatus.

9. The apparatus of claim 8, wherein the upper layer is pulled from the adhesive surface to expose the adhesive surface when the syringe apparatus is unpackaged.

10. The apparatus of claim 1, wherein the adhesive cup includes a concave surface.

11. The apparatus of claim 1, wherein the adhesive cup is flexible to allow for the adhesive cup to wrap around containers of different sizes with the application of pressure to the adhesive cup.

12. The medical syringe apparatus of claim 1, wherein the at least one interfacing member is mated to the medication container without the use of shape memory.

13. A medical syringe apparatus, comprising:
  a syringe unit; and
  at least one interfacing member for mating a labeled medication container to the syringe unit such that the medication label is visible and unobstructed and such that the container remains mated to the syringe when the syringe is in use,
  wherein the at least one interfacing member is an adhesive cup for receiving the container and accommodating containers of more than one size,
  wherein at least part of the adhesive cup is flexible and the adhesive cup includes an adhesive surface on the flexible part of the adhesive cup, and
  wherein an outer surface of the adhesive cup is substantially planar with respect to a plane of symmetry shared by the syringe unit and the mated medication container when the adhesive cup is in an open or unwrapped state.

14. The syringe apparatus of claim 13, additionally comprising:
  an indicator pad for changing a visual state when exposed to a change in ambient conditions.

15. The medical syringe apparatus of claim 13, wherein the at least one interfacing member is mated to the medication container without the use of shape memory.

16. A medical syringe apparatus, comprising:
  a syringe unit;
  a hypodermic needle attached to the syringe unit;
  at least one interfacing member for mating a labeled medication container to the syringe unit such that the medication label is visible and unobstructed and such that the container remains mated to the syringe when the syringe is in use, the interfacing member comprising an adhesive cup; and
  a sterile packaging covering the hypodermic needle and the interfacing member, having an upper layer and a lower layer with the upper layer pressed against an adhesive surface of the interfacing member such that when the sterile packaging is removed, the adhesive surface is exposed and ready to receive the medication container,
  wherein the adhesive cup does not completely surround the container 360 degrees, and
  wherein an outer surface of the adhesive cup is substantially planar with respect to a plane of symmetry shared by the syringe unit and the mated medication container when the adhesive cup is in an open or unwrapped state.

17. The medical syringe apparatus of claim 16, wherein the at least one interfacing member is mated to the medication container without the use of shape memory.

18. A medical syringe apparatus, comprising:
  a syringe unit; and
  at least one interfacing member for mating a labeled medication container to the syringe unit such that the medication label is visible and unobstructed and such that the container remains mated to the syringe when the syringe is in use,
  wherein the interfacing member is an adhesive cup for receiving the container,
  wherein the interfacing member has an adhesive surface for adhering to the container to irremovably attach the container to the interfacing member, and
  wherein an outer surface of the adhesive cup is substantially planar with respect to a plane of symmetry shared by the syringe unit and the mated medication container when the adhesive cup is in an open or unwrapped state.

19. The medical syringe apparatus of claim 18, wherein the at least one interfacing member is mated to the medication container without the use of shape memory.

20. A medical syringe apparatus, comprising:
a syringe unit; and
at least one interfacing member for mating a labeled medication container to the syringe unit such that the medication label is visible and unobstructed and such that the container remains mated to the syringe when the syringe is in use,
wherein the interfacing member is an adhesive cup for receiving the container,
wherein the adhesive cup does not completely surround the container 360 degrees, and
wherein an outer surface of the adhesive cup member is substantially planar with respect to a plane of symmetry shared by the syringe unit and the mated medication container when the adhesive cup is in an open or unwrapped state.

21. The medical syringe apparatus of claim 20, wherein the at least one interfacing member is mated to the medication container without the use of shape memory.

22. A medical syringe apparatus, comprising:
a syringe unit; and
at least one interfacing member for mating a labeled medication container to the syringe unit such that the medication label is visible and unobstructed and such that the container remains mated to the syringe when the syringe is in use,
wherein the at least one interfacing member is an adhesive cup for receiving the container and accommodates containers of more than one size,
wherein at least part of the adhesive cup is flexible and the adhesive cup includes an adhesive surface on the flexible part of the adhesive cup, and
wherein an outer surface of the adhesive cup is substantially planar with respect to a plane of symmetry shared by the syringe unit and the mated medication container when the adhesive cup is in an open or unwrapped state.

23. The medical syringe apparatus of claim 22, wherein the at least one interfacing member is mated to the medication container without the use of shape memory.

24. A medical syringe apparatus, comprising:
a syringe unit;
a hypodermic needle attached to the syringe unit; and
at least one interfacing member for mating a labeled medication container to the syringe unit, irrespective of the size of the container, such that the medication label is visible and unobstructed and such that the container remains mated to the syringe when the syringe is in use,
wherein the at least one interfacing member is mated to the medication container without the use of shape memory, and
wherein an outer surface of the at least one interfacing member is substantially planar with respect to a plane of symmetry shared by the syringe unit and the mated medication container when the at least one interfacing member is in an open or unwrapped state.

25. A medical syringe apparatus, comprising:
a syringe unit; and
at least one interfacing member for mating a labeled medication container to the syringe unit, irrespective of the size of the container, such that the medication label is visible and unobstructed and such that the container remains mated to the syringe when the syringe is in use,
wherein the at least one interfacing member is mated to the medication container without the use of shape memory, and
wherein an outer surface of the at least one interfacing member is substantially planar with respect to a plane of symmetry shared by the syringe unit when the at least one interfacing member is in an open or unwrapped state.

26. The apparatus of claim 25, additionally including an attachment unit for attaching a hypodermic needle to the medical syringe apparatus.

* * * * *